(12) United States Patent
Triva

(10) Patent No.: US 9,170,177 B2
(45) Date of Patent: Oct. 27, 2015

(54) DEVICE AND A METHOD FOR COLLECTING AND TRANSFERRING SAMPLES OF BIOLOGICAL MATERIAL

(71) Applicant: Copan Italia S.p.A., Brescia (IT)

(72) Inventor: Daniele Triva, Bovezzo (IT)

(73) Assignee: Copan Italia S.p.A., Brescia (IT)

( * ) Notice: Subject to any disclaimer, the term of this patent is extended or adjusted under 35 U.S.C. 154(b) by 353 days.

(21) Appl. No.: 13/661,376

(22) Filed: Oct. 26, 2012

(65) Prior Publication Data
US 2014/0083213 A1 Mar. 27, 2014

(30) Foreign Application Priority Data

Sep. 25, 2012 (IT) .......................... MI2012A001603

(51) Int. Cl.
*G01N 1/02* (2006.01)
*A61B 10/00* (2006.01)
*A61B 10/02* (2006.01)

(52) U.S. Cl.
CPC ............... *G01N 1/02* (2013.01); *A61B 10/0045* (2013.01); *A61B 2010/0216* (2013.01); *G01N 2001/028* (2013.01)

(58) Field of Classification Search
CPC ................ G01N 2001/028; G01N 2001/1056; A61B 2010/0074; A61B 2010/0216
See application file for complete search history.

(56) References Cited

U.S. PATENT DOCUMENTS

| | | | |
|---|---|---|---|
| 3,163,160 A | 12/1964 | Cohen | |
| 3,744,499 A | 7/1973 | Wells | |
| 3,900,651 A | 8/1975 | Hoppe et al. | |
| 4,030,978 A | 6/1977 | Abramson | |
| 4,039,934 A | 8/1977 | Ostashko et al. | |
| 4,326,545 A | 4/1982 | Motegi et al. | |

(Continued)

FOREIGN PATENT DOCUMENTS

| | | |
|---|---|---|
| CN | 1070850 | 4/1993 |
| CN | 2183735 | 11/1994 |

(Continued)

OTHER PUBLICATIONS

Print of website http://www.flock.de/de/2_1_historie.php, believed to be Jul. 22, 2008, and including what is believed to be an English counterpart to the website printed from Print of website in English http://www.flock.de/pages/html/de/flock/sub/historie.html?lang=EN.

(Continued)

*Primary Examiner* — Paul West
(74) *Attorney, Agent, or Firm* — Fish & Richardson P.C.

(57) ABSTRACT

A device (1) for collecting and transferring samples of biological material, where the device comprises at least: a support body (2) having at least a first end portion (2*a*) and at least a gripping portion (2*b*), and a plurality of fibers (6) attached to and arranged on the first portion (2*a*) of the support body (2) by flocking, such as to define a flocked collecting portion (3) suitable for collecting, on the collecting portion (3), a quantity of a sample of biological material, where the support body (2) is made of polyamide (PA or nylon), in particular polyamide 66 (PA66 or nylon 66). The support body can be provided with at least a weakened portion (4) suitable for enabling a selective breaking of the support body and a separation of the collecting portion (3) at least from a part of the gripping portion (2*b*).

21 Claims, 3 Drawing Sheets

(56) References Cited

U.S. PATENT DOCUMENTS

| | | | |
|---|---|---|---|
| 4,421,809 A | 12/1983 | Bish et al. | |
| 4,707,450 A | 11/1987 | Nason | |
| 4,719,181 A | 1/1988 | Schobel et al. | |
| 4,734,964 A * | 4/1988 | Lane et al. | 29/33 R |
| 4,749,655 A | 6/1988 | Monthony et al. | |
| 4,754,764 A | 7/1988 | Bayne | |
| 4,767,398 A | 8/1988 | Blasius, Jr. | |
| 4,861,343 A | 8/1989 | Neunzig | |
| 4,877,036 A | 10/1989 | Saint-Amand | |
| 4,877,037 A | 10/1989 | Ko et al. | |
| 4,922,936 A | 5/1990 | Buzzi et al. | |
| 5,009,846 A | 4/1991 | Gavet et al. | |
| 5,022,408 A | 6/1991 | Mohajer | |
| 5,091,153 A | 2/1992 | Bachand | |
| 5,163,441 A | 11/1992 | Monthony et al. | |
| 5,623,941 A | 4/1997 | Hedberg et al. | |
| 5,627,071 A | 5/1997 | Triva | |
| 5,704,388 A | 1/1998 | Freeman | |
| 5,738,643 A | 4/1998 | Stredic, III | |
| 5,944,519 A | 8/1999 | Griffiths | |
| 6,010,462 A | 1/2000 | Stoermer, III | |
| 6,232,567 B1 | 5/2001 | Bonino et al. | |
| 6,286,246 B1 | 9/2001 | Rachal et al. | |
| 6,352,513 B1 | 3/2002 | Anderson et al. | |
| 6,413,087 B1 | 7/2002 | Petrich et al. | |
| 6,420,181 B1 | 7/2002 | Novak | |
| 6,450,810 B1 | 9/2002 | Fischer et al. | |
| 6,494,856 B1 | 12/2002 | Zygmont | |
| 6,881,554 B2 | 4/2005 | DiCesare et al. | |
| 7,022,289 B1 | 4/2006 | Schlein et al. | |
| 8,114,027 B2 | 2/2012 | Triva | |
| 8,317,728 B2 | 11/2012 | Triva | |
| 2002/0001539 A1 | 1/2002 | DiCesare et al. | |
| 2002/0197738 A1 | 12/2002 | Matsumoto et al. | |
| 2003/0073932 A1 | 4/2003 | Varey | |
| 2003/0108846 A1 | 6/2003 | Hoertsch | |
| 2004/0014063 A1 | 1/2004 | Batteux et al. | |
| 2004/0158188 A1 | 8/2004 | Kauffmann et al. | |
| 2004/0197730 A1 | 10/2004 | Rowe et al. | |
| 2005/0181517 A1 | 8/2005 | Chandler et al. | |
| 2005/0288616 A1 | 12/2005 | Bozenbury, Jr. et al. | |
| 2006/0115805 A1 | 6/2006 | Hansen et al. | |
| 2006/0142668 A1 | 6/2006 | Triva | |
| 2007/0208274 A1 | 9/2007 | Ostrowski et al. | |
| 2007/0275101 A1 | 11/2007 | Lu et al. | |
| 2009/0024060 A1 | 1/2009 | Darrigrand et al. | |
| 2009/0030341 A1 | 1/2009 | Kshirsagar et al. | |
| 2010/0249649 A1 | 9/2010 | Larkin | |
| 2011/0281754 A1 | 11/2011 | Fischer et al. | |
| 2011/0306078 A1 | 12/2011 | Triva | |
| 2012/0150088 A1 | 6/2012 | Triva | |
| 2012/0171712 A1 | 7/2012 | Triva | |
| 2012/0271196 A1 | 10/2012 | Triva | |
| 2013/0072817 A1 | 3/2013 | Triva | |

FOREIGN PATENT DOCUMENTS

| | | |
|---|---|---|
| CN | 2460050 | 11/2001 |
| CN | 2479505 | 2/2002 |
| CN | 2554995 | 6/2003 |
| CN | 201131761 | 10/2008 |
| CN | 201993241 | 9/2011 |
| DE | 298 09 833 U1 | 6/1998 |
| DE | 10246379 A1 | 4/2004 |
| EP | 0 223 745 | 5/1987 |
| EP | 0 244 156 B1 | 4/1990 |
| EP | 0 643 131 A | 3/1995 |
| EP | 0 568 556 A1 | 7/1995 |
| EP | 0 707 836 A2 | 4/1996 |
| EP | 1 147 746 | 10/2001 |
| EP | 1 358 818 A1 | 11/2003 |
| GB | 406850 A | 3/1934 |
| JP | 05-027671 | 4/1993 |
| JP | 10-192050 | 7/1998 |
| JP | 2000-152817 | 6/2000 |
| JP | 2000342591 | 12/2000 |
| JP | 2001-346626 | 12/2001 |
| JP | 2002067201 | 3/2002 |
| JP | A-2004-587 | 1/2004 |
| WO | WO 89/10724 | 11/1989 |
| WO | WO 9212863 | 8/1992 |
| WO | WO 00/09984 | 2/2000 |
| WO | WO 00/54024 | 9/2000 |
| WO | WO 2004/086979 | 10/2004 |
| WO | 2005013759 | 2/2005 |
| WO | 2005110316 | 11/2005 |
| WO | WO 2007/075412 | 7/2007 |
| WO | WO 2008/131033 | 10/2008 |
| WO | 2009018607 | 2/2009 |
| WO | 2009140356 | 11/2009 |
| WO | WO 2009/134509 | 11/2009 |
| WO | WO 2009/136892 | 11/2009 |
| WO | WO 2009/158403 | 12/2009 |

OTHER PUBLICATIONS

BG-Information, BGI 764, p. 7, Oct. 2000, including translation from http://babelfish.yahoo.com/translate_txt, and further as a concise statement of relevance Applicant submits that the reference was cited in the European Notice of Opposition in EP 04 724 556.8, cited as item 46 herein.

Notice of Rejection for related Japanese patent application No. 2006-504927 (4 pages), mailed Feb. 15, 2009.

International Search Report (2 pages), for related international application WO 2004/086979, published Oct. 14, 2004.

File History for EP Application No. EP04724556, foreign counterpart to present application.

Print of Website www.swicofil.com/flock.html, believed to be Aug. 16, 2002.

"Flock 2003" Int. Flock Symposium, Apr. 2003, Dresden (3 pages).

Cotton—Facts and General Information from Swicofil, http:/lwww.swicofil.com/products/001cotton.html, Jan. 3, 2011, (9 pages).

Cotton—Wikipedia, the free encyclopedia, http://en.\wikipedia.org/wiki/Cotton, Jan. 3, 2011 (12pages).

MicroRheologics, "New Technology for Sample Collection" 2006, (2 pages).

Millipore, "Flocked Swabs" 2007, (2 pages).

What is Cotton Fibre/Properties of Cotton Fiber, http://articles.textileclass.com/cotton-fibre-what-is-cotton-fibre-cotton-f, May 11, 2011, (1 page).

Wikipedia, "Cotton Swab" http//en.wikipedia.org/wiki/Cotton swab, Jun. 22, 2011 (3 pages).

Wikipedia, "Swab" http://en.wikipedia.org/wiki/Swab, Jun. 22, 2011 (1 page).

International Search Report and Written Opinion for International Application No. IT MI20121603, mailed May 6, 2013, 8 pages.

* cited by examiner

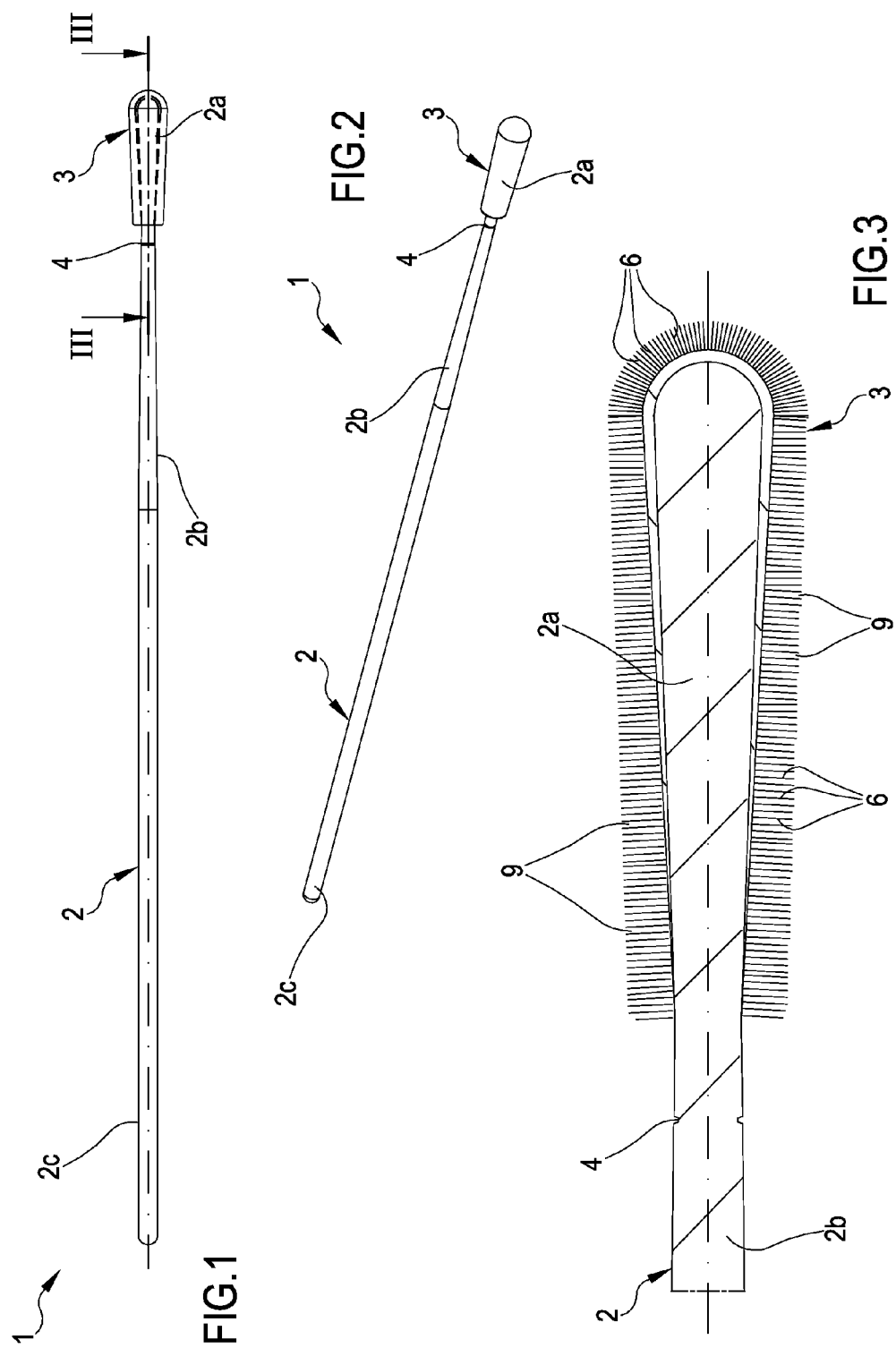

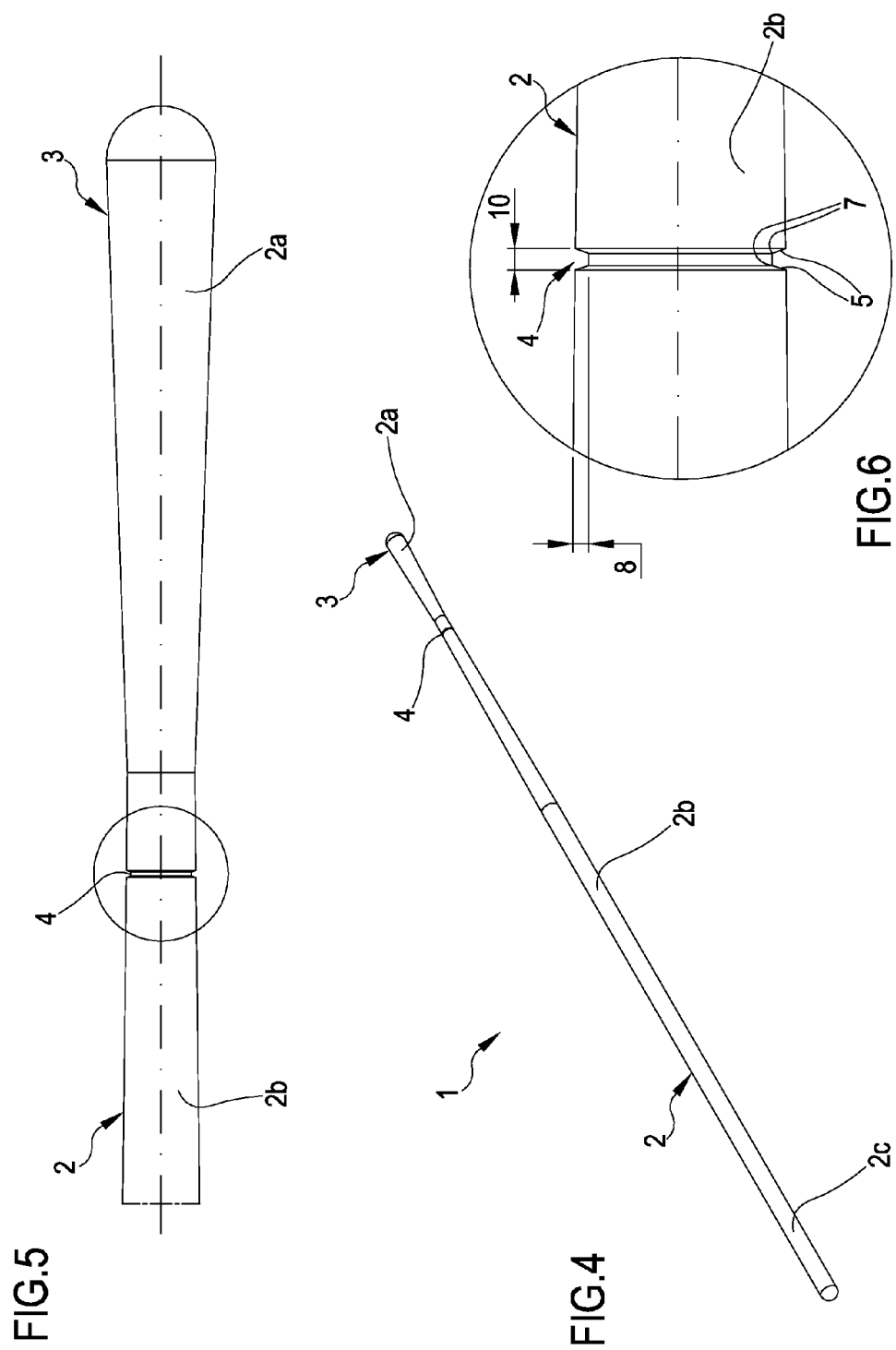

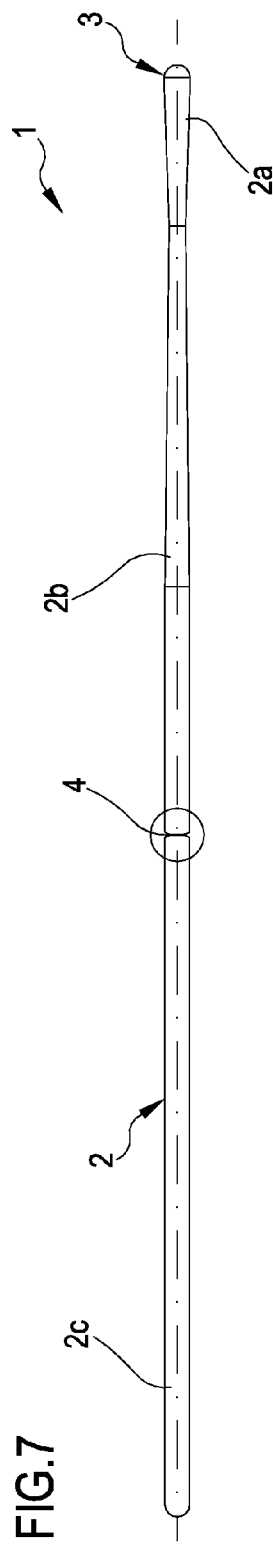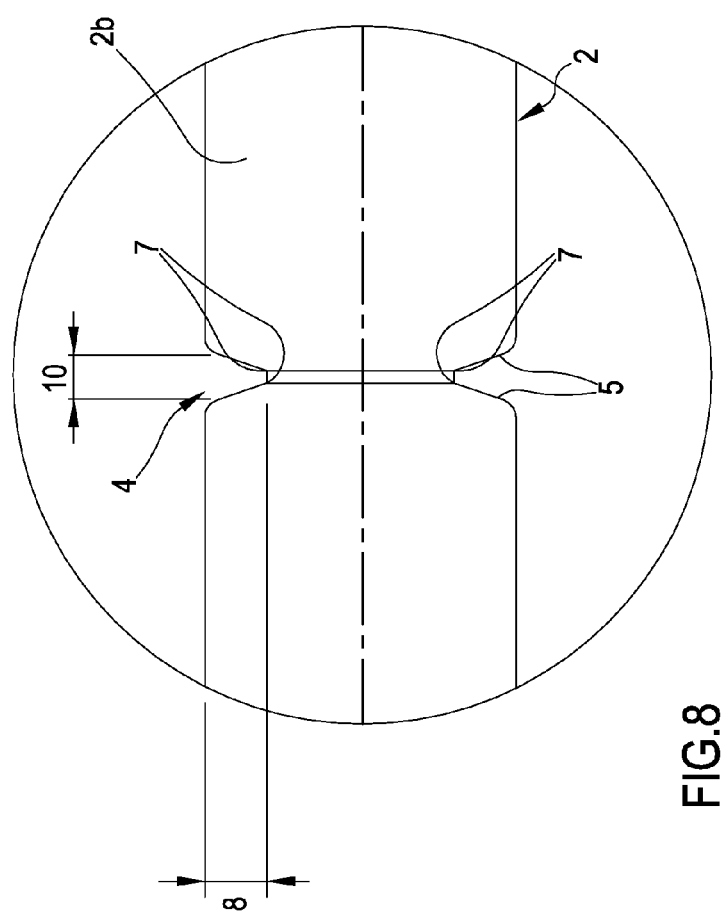
FIG.7
FIG.8

DEVICE AND A METHOD FOR COLLECTING AND TRANSFERRING SAMPLES OF BIOLOGICAL MATERIAL

CROSS REFERENCE TO RELATED APPLICATION

This claims priority under 35 U.S.C. §119 of Italian Application No. MI2012A001603 filed Sep. 25, 2012. Applicant incorporates the disclosure of all this application by reference herein.

DETAILED DESCRIPTION

The present invention relates to a device for collecting and transferring biological samples.

The invention further relates to a process for realising the device, a use of the device and a method for collecting and transferring samples of biological material by use of the device.

The device is for example applicable for collecting and transferring biological samples directly from the human body and in particular from human orifices, such as to enable, thereafter, conservation, transport and/or analysis of the samples.

In the prior art use is known of various types of collecting and transferring devices for analytes such as organic or biological substances, for example to subject subsequently to laboratory examination of analytical or diagnostic type. Swabs are known, for example, constituted by a rod at an end of which a cotton fibre is wound such as to define a collecting portion suitable for absorbing internally thereof the samples to be collected. These devices tend to retain the samples internally of the collecting portion and release only a small percentage thereof for analysis.

Also known, from patent JP4579902B2, are flocked swabs comprising an elongate support body and a plurality of flocked fibres at an end of the support body for defining a collecting portion for the analytes or biological samples. The flocked swabs enable release of a very high percentage of absorbed biological samples.

Both types of swabs described above exhibit elongate rods that are generally realised in flexible materials, for example polystyrene, and can therefore be subject to accidental breakage during use which can become problematic in particular in a case of collecting samples from human orifices.

A final point is that known-type swabs with breakable rods sometimes exhibit predetermined breaking points, suitable for enabling breakage of the rod at a precise and desired point with the aim of enabling conservation or transport of only the collecting portion, without the remaining gripping part.

Document JP2012016452A discloses a flocked swab realised in a more flexible and unbreakable material even if bent up to reaching a small radius of curvature, for example less than 4 mm, or preferably 3 mm or 2 mm, such as to obviate the drawback of accidental breakage.

The main aim of the present invention is to obviate one or more of the problems encountered in the prior art. Other aims of the present invention are to provide a method and a device for collecting and transferring biological samples which:
  exhibit a high flexibility of use and are adaptable to applications of considerably various type;
  enable avoiding undesired breakage of the rod;
  enable breaking the rod only in the presence of very specific and defined conditions;
  enable controlled breakage of the rod only in one or more precisely-determined points;
  exhibit great ease of use;
  exhibit high levels of reliability and safety in use;
  are simple and economical to realise.

These aims and more besides, which will more fully emerge from the following description, are substantially attained by a method and a device according to what is set out in one or more of the appended claims, taken alone or in combination. In a further aspect, the invention further relates to a process for producing a device according to any one of the accompanying claims comprising at least a step of producing the support body of the device having at least a first portion and a step of applying, by flocking, the plurality of fibres on the first portion, the process further comprising the step of realising, on the support body, at least a weakened portion by means of injection moulding of the support body or by means of a removal of material from the support body following the formation thereof. In a further aspect, the invention further relates to the use of a device, ad claimed, for collecting biological samples from a human body and/or a human orifice, in particular for collecting samples from the mouth, the pharynx, the nasal cavity, the eyes, the urethra, the vagina, the anus, the rectum or the skin. A detailed description now follows, by way of non-limiting example, of one or more preferred embodiments of the invention, in which:

FIG. 1 is a lateral view of a device according to a first embodiment of the present invention;

FIG. 2 is a perspective view of the device of FIG. 1;

FIG. 3 is a detail of the device of FIG. 1, relating to a flocked portion and a weakened portion;

FIG. 4 is a perspective view of a second embodiment of the present invention;

FIG. 5 is a detail of the device of FIG. 4, relating to a flocked portion and to a weakened portion;

FIG. 6 is a larger-scale representation of the weakened portion of FIG. 5;

FIG. 7 is a lateral view of a third embodiment of the present invention;

FIG. 8 is a larger-scale representation of the weakened portion of FIG. 7.

A description will now be made of a device 1 for collecting and transferring biological samples according to one or more embodiments of the invention. With reference to the accompanying figures of the drawings, 1 denotes in its entirety a device for collecting and transferring biological samples. The device 1 comprises a support body 2 which can have an elongate conformation and/or a substantially rod-shaped conformation. The support body 2 can have any section, even a variable section along the longitudinal section thereof. For example, the section can be circular, elliptical, or can have any other shape suitable for the purpose. In the invention, the support body 2 is made of polyamide (PA or nylon), in particular polyamide 66 (PA66 or nylon 66). The support body 2 can be bendable without breaking at least up to reaching a radius of curvature of 5 mm, or 4 mm or 3 mm or 2 mm or 1 mm. The support body 2 can be bendable without breaking for at least 10 cycles, or 20 cycles, or 50 cycles, or 100 cycles, or 200 cycles of 90° bending in opposite directions at ambient temperature of around 25° C. The support body 2 is provided with a first portion 2a, for example an end portion, defining a collecting portion 3 for the sample, a central second portion 2b, substantially rod-shaped and a third end portion 2c at which the rod can be gripped manually by an operator or which can be connectable to a further gripping element such as a cap for test tubes or the like. The collecting portion 3 for the sample can be conformed as a swab.

The collecting portion 3 is of the flocked type, realised by flocking of a plurality of fibres 6 on the first end 2a of the body. The flocked fibres 6 on the first end can be made of a hydrophilic material or a non-hydrophilic material, but the collecting portion 3 is in any case hydrophilic by capillarity thanks to the characteristics of the fibres 6 and the distribution thereof on the support body 2. In other terms, the collecting portion 3 can exhibit a continuous layer of fibres 6 made of a substantially adsorbent or non-absorbent material with respect to the sample, but conformed in an ordered plurality of capillary interstices 9 in which a predetermined quantity of the sample can be retained by imbibition, and from which it can be subsequently quantitatively released at the suitable moment, for example by rubbing the collecting portion 3 on a suitable release surface.

The depositing by flocking produces, on the end involved of the collecting device 1, a continuous and homogeneous layer of a plurality of fibres 6 having ordered arrangement, substantially perpendicular at any point to the first portion 2a of the support body 2 and each fibre of which is substantially parallel to the adjacent fibres 6. A corresponding ordered plurality of a capillary interstices 9 is defined between the fibres 6, in which a predetermined quantity of the sample can be collected and retained, including by imbibition due to the capillary effect. The flocked layer can thereafter effectively release the collected sample, for example by rubbing on a suitable surface or by dilution of the sample in a suitable diluent. The flocked collecting portion 3 can be configured and dimensioned such as to collect a suitable quantity of sample, for collecting a quantity of sample comprised for example between 5 and 1000 microliters, between 10 microliters and 500 microliters, or between 50 and 200 microliters, or between 80 and 120 microliters. The fibres 6 can be arranged on the support body 2 in a substantially ordered way and such as to form a substantially continuous layer on the collecting portion 3 and/or can be arranged on the collecting portion 3 such as to define a plurality of capillary interstices 9 suitable for adsorbing the sample by capillary action. The fibres 6 can exhibit a count comprised between 1 and 7 Dtex or between 1.7 and 3.3 Dtex, and/or a length comprised between 0.2 mm and 3 mm or between 0.6 mm and 2 mm. The fibres 6 can be arranged by flocking on the collecting portion 3 of the support body 2 with a surface density for example comprised between 50 and 500 fibres per $mm^2$ or between 100 and 200 fibres per $mm^2$ of surface of the first portion 2a of the support body 2. The fibres can be for example glued on the support body 2 by a vinyl adhesive. The layer of fibres can define an absorbent capacity for example of at least 0.5 µl per $mm^2$, or at least 0.6 µl per $mm^2$, or at least 0.7 µl per $mm^2$, or at least 0.75 µl per $mm^2$ of surface of the support body 2. The fibres can be realised in a substantially non-hydrophilic or non-adsorbent material towards the sample, and/or in a substantially hydrophilic or adsorbent material towards the sample and/or in a material selected from: polyamide (PA or nylon), rayon, polyester, carbon fibre, alginate, natural fibre, or a mixture of these materials. The fibres 6 are preferably made of nylon. The device 1 or the support body 2 can exhibit a longitudinal extension comprised between 50 mm and 200 mm or between 100 mm and 200 mm, 145 mm and 155 mm or between 148 mm and 152 mm or between 149 mm and 151 mm and/or a thickness or diameter in a perpendicular section to the central axis thereof, comprised between 0.8 mm and 5 mm or between 1 mm and 4 mm or between 2 mm and 3 mm or between 2.3 mm and 2.7 mm or between 2.4 mm and 2.6 mm. The support body 2 can further exhibit an intermediate connecting portion 2c at which it exhibits a diameter in perpendicular section to the longitudinal extension thereof comprised between 0.5 and 3 mm or between 1 mm and 2 mm or between 1.1 mm and 1.5 mm or between 1.2 mm and 1.4 mm.

The collecting portion 3 can exhibit a longitudinal extension comprised between 3 mm and 40 mm or between 13 mm and 22 mm or between 15 mm and 20 mm or between 16 mm and 19 mm and/or a diameter or thickness, comprising the fibres 6, comprised between 2 and 7 mm or between 3 mm and 6 mm or between 4.5 mm and 5.5 mm, or exhibits a diameter of the first portion, in perpendicular section to the longitudinal extension thereof, without the fibres, comprised between 1 mm and 6 mm or between 2 mm and 5 mm or between 3.5 mm and 4.5 mm. The collecting portion 3 can exhibit any suitable shape for the type of sample to be collected or the collecting seating, for example rounded or with one or more live edges. The support body 2 can be provided with a weakened portion 4, or a fracture point, suitable for facilitating a selective breaking of the support body 2 in an intermediate position between the first end and the second end, for example such as to facilitate the insertion of the first end and the second end, for example such as to facilitate the insertion of the collecting portion 3 in a transport container. The weakened portion 4 can be suitable for enabling a selective breaking of the support body 2 and a separation of the collecting portion 3 at least from a part of the gripping portion 2b. The weakened portion 4 can be configured to enable the selective breaking in the presence of a bending of the support body 2 at least on reaching a radius of curvature of 10 mm or 6 mm or 4 mm or 2 mm or 1 mm. The weakened portion 4 can be configured such as to enable the selective breaking in the presence of at least one, or one alone, complete bending of the support body on itself with an angle of less than 90° or 60° or 40° or 20° or 10° or 5°. The weakened portion can be conformed such that the two lateral walls 5 defined by the weakened portion enter into contact with one another, determining a lever effect able to cause the selective breaking, following a bending of the body in the presence of at least one, or one alone, total bending of the support body on itself with an angle of less than 90° or 60° or 40° or 20° or 10° or 5°. The weakened portion 4 can be configured such as not to enable the selective breaking in the presence of a bending of the support body with a radius of curvature of greater than 1 mm or 2 mm or 4 mm or 6 mm or 10 mm. The weakened portion 4 can be configured such as not to enable the selective breaking in the presence of at least one, or one alone, total bending of the support body on itself with an angle of greater than 2° or 5° or 10° or 20° or 30°. The weakened portion 4 can comprise a reduction in diameter of the support body 2 in perpendicular section to the longitudinal extension thereof of at least 0.1 mm or at least 0.2 mm or at least 0.4 mm or at least 0.8 mm or at least 1 mm. The weakened portion 4 can comprise a reduction in diameter of the support body in perpendicular section to the longitudinal extension thereof of at least 5% or at least 10% or at least 20% or at least 30% or at least 40% or at least 50%. To facilitate breakage, the depth 8 of the weakened portion can be at least 0.6 times the width 10 thereof on the surface of the support body, or at least 0.8 times its width, or at least equal to the width thereof, or can be at least 1.2 times the width thereof, or at least 1.5 times the width thereof. The weakened portion 4 can exhibit a substantially rounded conformation having a radius of curvature of less than 2 mm or 1 mm or 0.5 mm. The weakened portion 4 can exhibit a concave conformation and have at least a live edge 7, or at least two live edges 7, to facilitate breakage. The weakened portion can be for example realised by injection moulding of the support body 2. In a variant, the weakened portion 4 could be made, or finished, by a paring operation to remove material from the support body 2 following the formation thereof. The weakened portion 4 can be realised on the support body 2, on the gripping portion 2b or on an intermediate portion 2c between the gripping portion 2b and the collecting portion and/or in proximity of the collecting portion. The weakened portion 4 can be realised at a distance from the end of the flocked portion and the device comprised between 10 mm and 100 mm, or between 15 and 90 mm or between 20 mm and 80 mm. The collecting device 1 can comprise a plurality of support bodies 2, each provided with a collecting portion 3 having a conformation or a shape that is different and specifically configured for collecting a sample in a specific seating, or for collecting a specific quantity of sample. The collecting device 1 can further comprise a container for transporting the sample having an internal containing seating and an access opening. The container, not illustrated as of known type, can be a test tube for transporting samples of biological material or of biological origin. The collecting device 1 can further comprise a closing cap removably mountable at the access opening such as to selectively close the container. The container and/or closing cap can be made of a plastic material, for example polystyrol or polystyrene or polypropylene and/or of a suitable material for use with the specific sample to be collected, or in general suitable for use with biological materials or material of biological origin. The container and/or the closing cap and/or the support body 2 can be sterilised. The collecting device 1 can further comprise a sealed pack (not illustrated in the figures as in itself of known type) in which the support body 2 and/or the container and the closing cap can be housed before use for collecting a sample. The support body 2, the pack, the container and the cap can be sterile. The invention further relates to a use of the device described for collecting biological samples from a human body or a human orifice, in particular for collecting samples from the mouth, the pharynx, the nasal cavity, the eyes, the urethra, the vagina, the anus, the rectum or the skin. The invention further relates to a process for realising a device 1 of the above-described type. The process can for example comprise the following steps, of known type in themselves and therefore not described in greater detail: realising the support body 2, for example by injection moulding or by extrusion of polyamide (PA or nylon) in particular polyamide 66 (PA66 or nylon 66); applying a suitable glue to the first portion 2a of the body 2; applying the fibres 6 to the first portion 2a by flocking in an electromagnetic field; drying the glue in a suitable oven of tradition type such as to at least partially polymerise the glue. The invention further relates to a method for collecting and transferring biological samples by means of a device 1 of the above-described type. The method comprises at least a step of collecting a biological sample on at least a flocked collecting portion 3 of the collecting device 1, for example by inserting a flocked collecting portion 3 of the device in an orifice of the human body. The method can further comprise a step of conserving the sample on the collecting portion 3 for a predetermined amount of time. The method can further comprise the step of dehydrating or drying at least the collecting portion 3, provided with the collected sample. The step of drying can be performed for example by drying in an oven or by forced ventilation, or by means of other methods in themselves of known type and suitable for treatment of the sample. The method can further comprise the steps of inserting the collecting portion 3 in a vacuum container (or known type and therefore not illustrated in the figures) and of generating a substantial vacuum in the vacuum container. The step of generating the vacuum can be performed during the drying step, or at another moment, separately from the drying step. The method can further comprise the step of rehydrating the sample on the collecting portion 3, for example by means of at least a hydrating solution, such as to obtain a predetermined quantity of rehydrated sample on the collecting portion 3. The method can further comprise the steps of inserting the collecting portion 3, provided with the sample, in a container such as for example a test tube, closing the container by means of a cap or closing lid, and transferring the container comprising the collecting portion 3 and/or the step of predisposing in the container a predetermined quantity of a substance suitable for liquefaction and/or for the conservation of the sample and/or the step of agitating, shaking or rotating the container comprising the collecting portion 3 with the sample at a predetermined velocity and aimed at liquefying the sample. The method can further comprise the step of releasing the biological sample from the collecting portion in order to enable analytical operations on the sample. The method can in particular comprise the step of releasing at least 80%, or at least 85%, or at least 90% of the collected biological sample, by means of dilution in a liquid terrain or a dilutant buffer in order to enable the performing of further operations on the sample. The release can be facilitated using conventional rubbing operations. The present invention enables obtaining one or more of the following advantages. Firstly, the invention enables realising a process, a device realised according to the process, and a method for using the device that is able to obviate the drawbacks encountered in the prior art. In particular the invention further enables realising flocked swabs with great flexibility of use and easily adaptable to applications that can differ widely in type. The invention further enables avoiding undesired breakage of the rod of the swab, and at the same time enables the rod to be broken only in the presence of very precise and defined conditions, as well as only at one or more well-determined points. The swabs of the invention further exhibit great ease of use as well as high levels of reliability and safety of use. Lastly, the invention is simple and economical to actuate.

The invention claimed is:

1. A device for collecting and transferring samples of biological material, wherein the device comprises at least:
a support body having at least a first end portion a connecting intermediate portion exhibiting a diameter in perpendicular section to the longitudinal extension thereof comprised between 0.5 and 3 mm, and at least a gripping portion exhibiting a diameter in perpendicular section to the longitudinal extension that is comprised between 0.8 mm and 5 mm, the support body being bendable without breaking at least up to reaching a radius of curvature of 3 mm; and
a plurality of fibres attached to and arranged on said first end portion of said support body by flocking such as to define a plurality of capillary interstices apt to adsorb the sample by capillarity, for defining a flocked collecting portion exhibiting a length comprised between 3 mm and 40 mm and a diameter in perpendicular section to the longitudinal extension thereof, including the length of the fibres, comprised between 2 and 7 mm, the flocked collecting portion being apt to collect, on said collecting portion, a quantity of a sample of biological material by capillarity, wherein said fibres exhibit a count comprised between 1 and 7 dtex and a length comprised between 0.2 mm and 3 mm and wherein the support body is made of polyamide (PA or nylon) and wherein the flocked collecting portion (3) is configured for collecting by capillarity a quantity comprised between 50 and 200 microliters of the sample.

2. The device of claim 1, wherein said support body is bendable without breaking at least up to reaching a radius of curvature of 2 mm or of 1 mm and/or wherein said support body is bendable without breaking in correspondence of at least 10 cycles, or 20 cycles, or 50 cycles, or 100 cycles or 200 cycles of bending by 90° in opposite directions at ambient temperature of about 25° C.

3. The device of claim 1, wherein said support body is provided with at least a weakened portion apt to enable a selective breaking of the support body and a separation of said collecting portion at least from a part of said gripping portion.

4. The device of claim 3 in which said weakened portion is configured for enabling said selective breaking in the presence of a bending of said support body at least on reaching a radius of curvature of 10 mm or 6 mm or 4 mm or 2 mm or 1 mm and/or for enabling said selective breaking in the presence of at least one, or one alone, complete bending of said support body on itself with an angle of less than 90° or 60° or 40° or 20° or 10° or 5°.

5. The device of claim 3 in which the weakened portion is conformed such that two lateral walls defined by the weakened portion enter into mutual contact, determining a lever effect able to cause such selective breaking, following a bending of the body in a presence of at least one, or one alone, complete bending of said support body on itself at an angle of less than 90° or 60° or 40° or 20° or 10° or 5°.

6. The device of claim 3, wherein said weakened portion is configured such as not to enable said selective breaking in a presence of a bending of said support body with a radius of curvature of greater than 1 mm or 2 mm or 4 mm or 6 mm or 10 mm and/or such as not to enable said selective breaking in a presence of at least one, or one alone, complete bending of the support body on itself with an angle of greater than 2° or 5° or 10° or 20° or 30°.

7. The device of claim 3, wherein said weakened portion comprises a reduction of diameter of said support body perpendicular in section to its longitudinal extension of at least 0.1 mm or at least 0.2 mm or at least 0.4 mm or at least 0.8 mm, or at least 1 mm and/or a reduction in diameter of the support body perpendicular in section to its longitudinal extension of at least 5% or at least 10% or at least 20% or at least 30% or at least 40% or at least 50%.

8. The device of claim 3 wherein said weakened portion exhibits a substantially rounded conformation having a radius of curvature of less than 2 mm or 1 mm or 0.5 mm.

9. The device of claim 3 wherein said weakened portion exhibits a concave conformation and has at least a live edge such as to facilitate the breakage.

10. The device of claim 3 wherein the depth of the weakened portion can be at least 0.6 times a width thereof on the surface of the support body, or at least 0.8 times the width thereof, or can be at least equal to the width thereof, or can be at least 1.2 times the width thereof, or at least 1.5 times the width thereof.

11. The device of claim 3, wherein said weakened portion is realised by injection moulding of said support body or by means of removal of material from the support body following the formation thereof.

12. The device of claim 3 wherein said weakened portion is realised on said support body on said gripping portion or on an intermediate portion between said gripping portion and said collecting portion and/or is realised in proximity of said collecting portion and/or is realised at a distance from the end of said flocked portion and of said device comprised between 10 mm and 100 mm, or between 15 and 90 mm or between 20 mm and 80 mm.

13. The device of claim 1, wherein said support body exhibits a length, in a longitudinal extension thereof, comprised between 50 mm and 200 mm or between 100 mm and 200 mm, 145 mm and 155 mm or between 148 mm and 152 mm or between 149 mm and 151 mm and/or exhibits, in correspondence of the gripping portion, a diameter in perpendicular section to the longitudinal extension that is comprised between 1 mm and 4 mm or between 2 mm and 3 mm or between 2.3 mm and 2.7 mm or between 2.4 mm and 2.6 mm.

14. The device of claim 1 wherein said support body exhibits a connecting intermediate portion in correspondence of which it exhibits a diameter in perpendicular section to the longitudinal extension thereof comprised between 1 mm and 2 mm or between 1.1 mm and 1.5 mm or between 1.2 mm and 1.4 mm.

15. The device of claim 1 wherein said support body exhibits a length of the flocked collecting portion comprised between 13 mm and 22 mm or between 15 mm and 20 mm or between 16 mm and 19 mm and/or exhibits a diameter of the flocked collecting portion, in perpendicular section to the longitudinal extension thereof, including the length of the fibres, comprised between 3 mm and 6 mm or between 4.5 mm and 5.5 mm and/or exhibits a diameter of the first end portion, in perpendicular section to the longitudinal extension thereof, without the fibres, comprised between 1 mm and 6 mm or between 2 mm and 5 mm or between 3.5 mm and 4.5 mm.

16. The device of claim 1, wherein said flocked collecting portion is configured for collecting a substantially known quantity of said sample, or for collecting a quantity comprised between between 80 and 120 microliters of said sample, and/or for collecting a sample quantity of at least 0.5 µl per $mm^2$, or of at least 0.6 µl per $mm^2$, or of at least 0.7 µl per $mm^2$, or of at least 0.75 µl per $mm^2$, and/or wherein said fibres are arranged on said first end portion of said support body in a substantially ordered way and in such a way as to form a substantially continuous layer on said collecting portion.

17. The device of claim 1, wherein said fibres exhibit a count comprised between 1.7 and 3.3 Dtex, and/or a length comprised between 0.6 mm and 2 mm.

18. The device of claim 1 wherein said fibres are realised in polyamide (PA or nylon) or in a material selected from among: rayon, polyester, carbon fibre, alginate, natural fibre, or a mixture of these materials and/or wherein said fibres are attached to said first portion by means of a vinyl adhesive.

19. The device of claim 1 wherein said support body is realised by injection moulding or by extrusion and/or wherein said collecting portion exhibits a surface density of said fibres on said collecting portion comprised between 50 and 500 fibres per $mm^2$ or between 100 and 200 fibres per $mm^2$.

20. A method for collecting and transferring samples of biological material by means of a device according to claim 1, the method comprising at least the steps of:
inserting a flocked collecting portion of said device in an orifice of the human body and collecting a biological sample on said flocked collecting portion of the collecting device having a support body,
conserving said sample on said collecting portion for a time period and/or
releasing said biological sample from said collecting portion in order to enable performing analytical operations on said sample.

21. The device of claim 1 wherein said support body is made of polyamide 66 (PA66 or nylon 66).

* * * * *